United States Patent
Lee et al.

(10) Patent No.: US 12,178,590 B2
(45) Date of Patent: Dec. 31, 2024

(54) MUSCLE CONTROL DEVICE AND OPERATION METHOD THEREOF

(71) Applicant: ELECTRONICS AND TELECOMMUNICATIONS RESEARCH INSTITUTE, Daejeon (KR)

(72) Inventors: Dong Woo Lee, Daejeon (KR); Jabeom Gu, Sejong-si (KR); Baesun Kim, Daejeon (KR); Yong Ki Son, Sejong-si (KR); Joonyoung Jung, Daejeon (KR); Hyung Cheol Shin, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 17/641,828

(22) PCT Filed: Feb. 19, 2021

(86) PCT No.: PCT/KR2021/002127
§ 371 (c)(1),
(2) Date: Mar. 10, 2022

(87) PCT Pub. No.: WO2021/182765
PCT Pub. Date: Sep. 16, 2021

(65) Prior Publication Data
US 2024/0041384 A1  Feb. 8, 2024

(30) Foreign Application Priority Data

Mar. 10, 2020 (KR) .......... 10-2020-0029780
Dec. 10, 2020 (KR) .......... 10-2020-0172371

(51) Int. Cl.
*A61N 1/04* (2006.01)
*A61B 5/389* (2021.01)
*A61N 1/36* (2006.01)

(52) U.S. Cl.
CPC ............ *A61B 5/389* (2021.01); *A61N 1/0408* (2013.01); *A61N 1/36003* (2013.01); *A61B 2562/0219* (2013.01)

(58) Field of Classification Search
CPC ... A61B 5/389; A61B 2562/0219; A61B 5/00; A61N 1/0408; A61N 1/36003;
(Continued)

(56) References Cited

U.S. PATENT DOCUMENTS 10,390,756 B2   8/2019  Youm et al.
2014/0163444 A1*  6/2014  Ingvarsson ........ A61N 1/36003
                                                          602/2
(Continued)

FOREIGN PATENT DOCUMENTS

JP    2018-175020 A    11/2018
JP    2020-505199 A    2/2020
(Continued)

OTHER PUBLICATIONS

Search Report, mailed Jun. 4, 2021, for International Application No. PCT/KR2021/002127.
(Continued)

*Primary Examiner* — Yingchuan Zhang
*Assistant Examiner* — Anh-Khoa N Dinh
(74) *Attorney, Agent, or Firm* — LRK PATENT LAW FIRM

(57) ABSTRACT

A muscle control device includes an electromyography (EMG) electrode unit including a plurality of electrodes, and that senses an EMG signal, an EMG circuit unit that generates channel data, based on electrode signals, a control
(Continued)

unit that receives the channel data, extracts a volitional electromyography signal, based on the channel data, and determines FES (Functional Electrical Stimulation) stimulation parameters, based on the volitional electromyography signal, an FES electrode unit that outputs a functional electrical stimulation, based on the FES stimulation parameters, and an FES circuit unit that receives the FES stimulation parameters, generates the functional electrical stimulation, based on the FES stimulation parameters, and transmits the functional electrical stimulation to the FES electrode unit, and the control unit recognizes a direction and an intensity of a motion from the volitional electromyography signal, based on the volitional electromyography signal and adjusts an intensity of the functional electrical stimulation.

14 Claims, 15 Drawing Sheets

(58) Field of Classification Search
CPC .......... A61N 1/02; A61N 1/04; A61N 1/0452; A61N 1/36; A61N 1/36031; A61N 1/36034; A61N 1/0456; A61N 1/0476; A61N 1/36067; A61N 1/0484; A61N 1/0504; A61N 1/0551; A61N 1/36014; A61N 1/36017; A61N 1/3603; A61N 1/36062; A61N 1/36135; A61N 1/36139; A61N 1/025; A61N 1/36036

See application file for complete search history.

(56) References Cited

U.S. PATENT DOCUMENTS

| | | | |
|---|---|---|---|
| 2016/0144172 A1* | 5/2016 | Hsueh | A61B 5/389 607/48 |
| 2017/0224985 A1* | 8/2017 | Debur | A61N 1/0452 |
| 2018/0200520 A1* | 7/2018 | Tranchina | A61N 1/36139 |
| 2019/0083002 A1 | 3/2019 | Jang et al. | |
| 2019/0200891 A1 | 7/2019 | Jung et al. | |
| 2020/0129753 A1 | 4/2020 | Liu et al. | |
| 2020/0139115 A1 | 5/2020 | Verity | |
| 2021/0128904 A1 | 5/2021 | Terekhov | |

FOREIGN PATENT DOCUMENTS

| | | |
|---|---|---|
| KR | 10-0546485 B1 | 1/2006 |
| KR | 10-2010-0079350 A | 7/2010 |
| KR | 10-2012-0057081 A | 6/2012 |
| KR | 10-2016-0119515 A | 10/2016 |
| KR | 10-2018-0109750 A | 10/2018 |
| KR | 10-2019-0032925 A | 3/2019 |
| KR | 10-2019-0041239 A | 4/2019 |
| KR | 10-2019-0083611 A | 7/2019 |
| KR | 10-2019-0090156 A | 8/2019 |
| KR | 10-2050261 B1 | 11/2019 |

OTHER PUBLICATIONS

Written Opinion, mailed Jun. 4, 2021, for International Application No. PCT/KR2021/002127.
Dongwoo Lee, "ETRI develops wearable walking assistance system for the elderly", Article, Jul. 23, 2020.
Shin, Hyeong-Cheol et al. "ETRI wearable walking assistance system", Human Augmentation Lab, 2020.

* cited by examiner

MUSCLE CONTROL DEVICE AND OPERATION METHOD THEREOF

CROSS-REFERENCE TO RELATED APPLICATIONS

The present application is a U.S. National Phase entry from International Application No. PCT/KR2021/002127, filed on Feb. 19, 2021, which claims priority to Korean Patent Application No. 10-2020-0029780, filed on Mar. 10, 2020, and No. 10-2020-0172371, filed on Dec. 10, 2020, the disclosure of which is incorporated by reference herein in their entirety.

TECHNICAL FIELD

The present disclosure relates to a muscle control device, and more particularly, relates to a muscle control device and an operation method thereof.

BACKGROUND ART

When an electrical stimulation is applied to a neuromuscular, a muscle contracts. An electrical muscle stimulation (EMS) using this principle is used in the field to obtain an exercise effect by using muscle contraction due to the electrical stimulation. A functional electrical stimulation (FES) is used in the field of technology to make joint movements and perform special functions (e.g., lifting, grabbing, walking, raising, etc.) by applying the electrical stimulation to the neuromuscular to contract the muscle.

The FES has been used in the field of rehabilitation for patients with paralysis or partial paralysis due to a disease such as stroke since the 1960s. The FES may generate natural motion by properly reflecting a user's motion intention. To identify the user's motion intention, an EEG or an EMG is used. In identifying the user's motion intention using the EMG, a problem arises that the EMG and the FES cannot be used at the same time due to signal interference of the FES.

DISCLOSURE

Technical Problem

The problem to be solved by the present disclosure is to provide a muscle control device that uses an FES reflecting a user's intention (a direction of a motion, a strength of a force) and an operation method thereof.

Technical Solution

The muscle control device according to an embodiment of the present disclosure includes an electromyography (EMG) electrode unit including a plurality of electrodes, and that senses an EMG signal, an EMG circuit unit that generates channel data, based on electrode signals received from the EMG electrode unit, a control unit that receives the channel data from the EMG circuit unit, extracts a volitional electromyography signal, based on the channel data, and determines FES (Functional Electrical Stimulation) stimulation parameters, based on the volitional electromyography signal, an FES electrode unit that outputs a functional electrical stimulation, based on the FES stimulation parameters, and an FES circuit unit that receives the FES stimulation parameters from the control unit, generates the functional electrical stimulation, based on the FES stimulation parameters, and transmits the functional electrical stimulation to the FES electrode unit, and the control unit adjusts an intensity of the functional electrical stimulation, based on the volitional electromyography signal.

In an embodiment, the control unit may generate an EMG effective value by performing a root mean square operation on the volitional electromyography signal, and may determine the FES stimulation parameters such that the intensity of the functional electrical stimulation increases as the EMG effective value increases.

In an embodiment, values of the FES stimulation parameters may be proportional or inversely proportional to the EMG effective value.

In an embodiment, the FES stimulation parameters may be any one of a pulse magnitude, a pulse period, a pulse width, or a pulse shape.

In an embodiment, the muscle control device may identify a user's intention including a direction of a motion or a strength of a force, based on the volitional electromyography signal.

In an embodiment, the control unit may communicate with the EMG circuit unit and the FES circuit unit, based on any one of a UART (universal asynchronous receiver-transmitter), an SPI (serial peripheral interface), an I2C (inter-integrated circuit), a Bluetooth, a USB (Universal Serial Bus), or a WiFi.

In an embodiment, the channel data may include first channel data and second channel data, and the control unit may extract first channel previous period data and second channel previous period data during a first period, may extract first channel current period data and second channel current period data during a second period, may generate first channel difference calculation data by performing a difference calculation on the first channel previous period data and the first channel current period data, may generate second channel difference calculation data by performing a difference calculation on the second channel previous period data and the second channel current period data, and may extract the volitional electromyography signal by performing a difference calculation on the first channel difference calculation data and the second channel difference calculation data.

In an embodiment, the EMG signal may be a signal in which a stimulation artifact, an M-wave, which are caused by the functional electrical stimulation, and the volitional electromyography signal are combined.

A method of operating a muscle control device according to an embodiment of the present disclosure includes sensing an EMG (Electromyography) signal through a plurality of electrodes, extracting a volitional electromyography signal based on the EMG signal, determining whether a user is performing a periodic action, adjusting an FES (Functional Electrical Stimulation) time when it is determined that the user is performing the periodic action, determining FES stimulation parameters based on the volitional electromyography signal, and outputting a functional electrical stimulation, based on the FES stimulation parameters, and an intensity of the functional electrical stimulation is adjusted based on the volitional electromyography signal.

In an embodiment, the determining of the FES stimulation parameters based on the volitional electromyography signal may include generating an EMG effective value by performing a root mean square operation on the volitional electromyography signal, and determining values of the FES stimulation parameters to be proportional to the EMG effective value.

In an embodiment, a relatively large EMG effective value may indicate an intention of the user to move a joint by applying a lot of force, and a relatively small EMG effective value may indicate an intention of the user to move the joint by applying a small force.

In an embodiment, the determining of the FES stimulation parameters based on the volitional electromyography signal may further include when the EMG effective value is relatively large, adjusting values of the FES stimulation parameters such that the intensity of the functional electrical stimulation is large, and when the EMG effective value is relatively small, adjusting the values of the FES stimulation parameters such that the intensity of the functional electrical stimulation is small.

In an embodiment, the adjusting of the FES time may include adjusting the FES time to precede a time of the EMG signal.

In an embodiment, the extracting of the volitional electromyography signal based on the EMG signal may include removing effects of a stimulation artifact and an M-wave which are generated by the functional electrical stimulation from the sensed EMG signal.

In an embodiment, the adjusting of the FES time may include adjusting the FES time, based on information acquired using a foot switch, an inertia measurement unit (IMU) sensor, or a goniometer.

Advantageous Effects

According to an embodiment of the present disclosure, in controlling muscles with the FES, a muscle control device may assist in performing a natural motion by identifying a motion intention in real time through the EMG signal and controlling a muscle according to the motion intention. Accordingly, an improved muscle control device and a method of operating the same are provided.

BEST MODE

Figure 1:
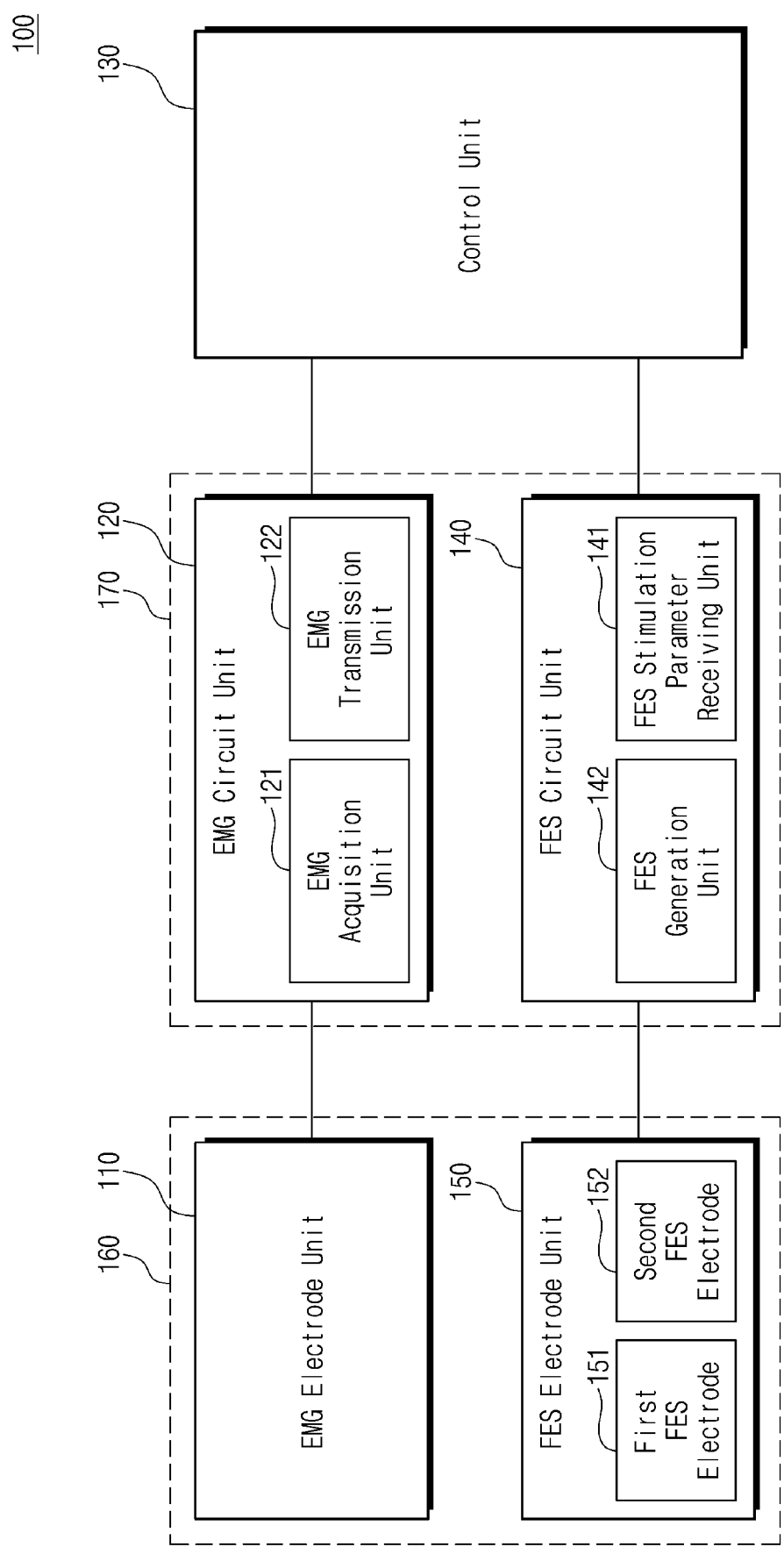
FIG. 1 is a block diagram illustrating a muscle control device according to an embodiment of the present disclosure.

FIG. 1 is a diagram representing the best mode for carrying out the present disclosure.

MODE FOR INVENTION

Hereinafter, embodiments of the present disclosure will be described clearly and in detail such that those skilled in the art may easily carry out the present disclosure.

FIG. 1 is a block diagram illustrating a muscle control device according to an embodiment of the present disclosure. Referring to FIG. 1, a muscle control device 100 may include an electromyography (EMG) electrode unit 110, an EMG circuit unit 120, a control unit 130, a functional electrical stimulation (FES) circuit unit 140, and an FES electrode unit 150. In an embodiment, the muscle control device 100 may be attached or worn on the user's body. The muscle control device 100 may apply a load to a user's rehabilitation exercise or may assist the user's rehabilitation exercise. The muscle control device 100 of the present disclosure is not necessarily limited to being used only for the user's rehabilitation exercise, but may be used to strengthen muscles or improve physical functions such as a walking operation, an object lifting operation, a stair climbing operation, etc.

The muscle control device 100 may sense an electromyogram (or muscle activity) (EMG) signal to identify a motion intention. For example, the EMG technology may measure a degree of muscle activity by measuring the potential difference that occurs in muscle cells when the muscle is activated. The EMG technology is widely used not only in the medical field but also in the biomechanics field. The EMG technology may measure the potential difference of muscles activated through electrodes attached to a skin surface.

The muscle control device 100 may sense the EMG signal to identify the motion intention, and accordingly may transfer an electrical signal to the neuromuscular to supplement and replace a function of a weakened muscle or a lost muscle. In other words, the functional electrical stimulation (FES) technology may contract the muscle by applying electrical stimulation to the neuromuscular. Due to this, the FES technology may assist in making joint movement and performing special functions (e.g., lifting, grabbing, walking, raising, etc.).

The muscle control device 100 may identify the user's motion intention in real time and may control the muscle accordingly. That is, the muscle control device 100 may be an EMG-controlled FES equipment. The EMG-FES equipment may be classified into an EMG-triggered FES equipment and the EMG-controlled FES equipment. Problems may arise when using an EMG and an FES at the same time. For example, since the FES is an electrical signal greater than that of the EMG, distortion may occur when measuring the EMG signal due to interference of the FES signal. Therefore, the EMG-triggered FES equipment may be mainly used.

The EMG-triggered FES equipment may measure the EMG signal before applying the FES. When the EMG signal greater than or equal to a specific threshold is detected, the EMG-triggered FES may apply the electrical stimulation to the neuromuscular for a predetermined time. The user using the EMS-triggered FES equipment may feel unnatural when trying to make joint movements that relax muscles during the electrical stimulation. That is, the EMS-triggered FES equipment has a problem in that it is difficult to provide natural muscle control in accordance with the user's motion intention.

On the other hand, the EMG-controlled FES equipment may measure the EMG signal in real time and may reflect it to adjust the electrical stimulation applied to the neuromuscular. That is, the muscle control device 100 may provide natural muscle control by simultaneously using the EMG signal and the FES together.

The EMG electrode unit 110 may be configured to sense or detect the EMG signal. For example, the EMG electrode unit 110 may detect the EMG signal or an EMG electrode signal through a plurality of electrodes and may transmit the same to the EMG circuit unit 120. For example, the EMG electrode unit 110 may include a plurality of electrodes that sense the EMG signal for one control target muscle. The structure and more detailed description of the EMG electrode unit 110 will be described with reference to FIGS. 2A and 2B.

The EMG circuit unit 120 may convert the EMG signal sensed through the EMG electrode unit 110 into digital data, and then transfer the digital data to the control unit 130. The EMG circuit unit 120 may include an EMG acquisition unit 121 and an EMG transmission unit 122.

The EMG acquisition unit 121 may receive the EMG electrode signal sensed through the EMG electrode unit 110. The EMG acquisition unit 121 may convert the EMG electrode signal, which is an analog signal, into the digital data. The EMG transmission unit 122 may identify the digital data provided from the EMG acquisition unit 121 for each channel and may transmit an EMG channel data to the control unit 130.

In an embodiment, the EMG transmission unit 122 may communicate with the control unit 130, based on various communication protocols such as a universal asynchronous receiver-transmitter (UART), a serial peripheral interface (SPI), an inter-integrated circuit (I2C), a Bluetooth, a universal serial bus (USB), a WiFi, etc.

The control unit 130 may identify the user's motion intention and may determine FES stimulation parameters. For example, the control unit 130 may extract an EMG effective value (RMS: root mean square) from the EMG channel data to identify the motion intention, and may determine the FES stimulation parameters to match the motion intention. The user's motion intention may include a direction of a motion, a strength of a force, etc.

In an embodiment, the control unit 130 may receive first and second channel data from the EMG circuit unit 120. The control unit 130 may extract a volitional electromyography (vEMG) signal or vEMG data, based on the first and second channel data. A more detailed description of the volitional electromyography signal will be described in FIGS. 3 and 5. The control unit 130 may generate the EMG effective value (RMS) by performing an operation on the volitional electromyography (vEMG) signal. The control unit 130 may determine the FES stimulation parameters, based on the volitional electromyography (vEMG) signal. The control unit 130 may provide the FES stimulation parameters to the FES circuit unit 140. The structure and more detailed description of the control unit 130 will be described in FIG. 3.

The FES circuit unit 140 may generate a functional electrical stimulation (FES), based on the FES stimulation parameters provided from the control unit 130. The FES circuit unit 140 may include an FES stimulation parameter receiving unit 141 and an FES generation unit 142. The FES stimulation parameter receiving unit 141 may receive the FES stimulation parameters from a FES stimulation parameter transmission unit 134. The FES stimulation parameter receiving unit 141 may provide the received FES stimulation parameters to the FES generation unit 142. The FES generation unit 142 may generate the functional electrical stimulation (FES), based on the FES stimulation parameters. The FES generation unit 142 may transmit the functional electrical stimulation (FES) to the FES electrode unit 150.

In an embodiment, the FES stimulation parameter receiving unit 141 may communicate with the control unit 130, based on various communication protocols such as the universal asynchronous receiver-transmitter (UART), the serial peripheral interface (SPI), the inter-integrated circuit (I2C), the Bluetooth, the universal serial (USB) Bus), the WiFi, etc.

The FES electrode unit 150 may be configured to transfer the electrical signal or the electrical stimulation to the neuromuscular. In an embodiment, the FES electrode unit 150 may include the plurality of electrodes that transfer the electrical stimulation to one control target muscle. The FES electrode unit 150 may include a first FES electrode 151 and a second FES electrode 152. The FES electrode unit 150 may transfer the FES received from the FES circuit unit 140 to the neuromuscular. The FES electrode unit 150 may induce a contraction of the control target muscle by transferring the FES to the neuromuscular.

In an embodiment, when the electrical energy transferred to the neuromuscular is large, the FES electrode unit 150 may assist the user to exert a large force by increasing the degree of contraction of the muscle. When the electrical energy transferred to the neuromuscular is small, the FES electrode unit 150 may assist the user to exert a small amount of force by reducing the degree of contraction of the muscle.

An electrode unit 160 may include the EMG electrode unit 110 and the FES electrode unit 150. A circuit board unit 170 may include the EMG circuit unit 120 and the FES circuit unit 140.

Figure 2A:
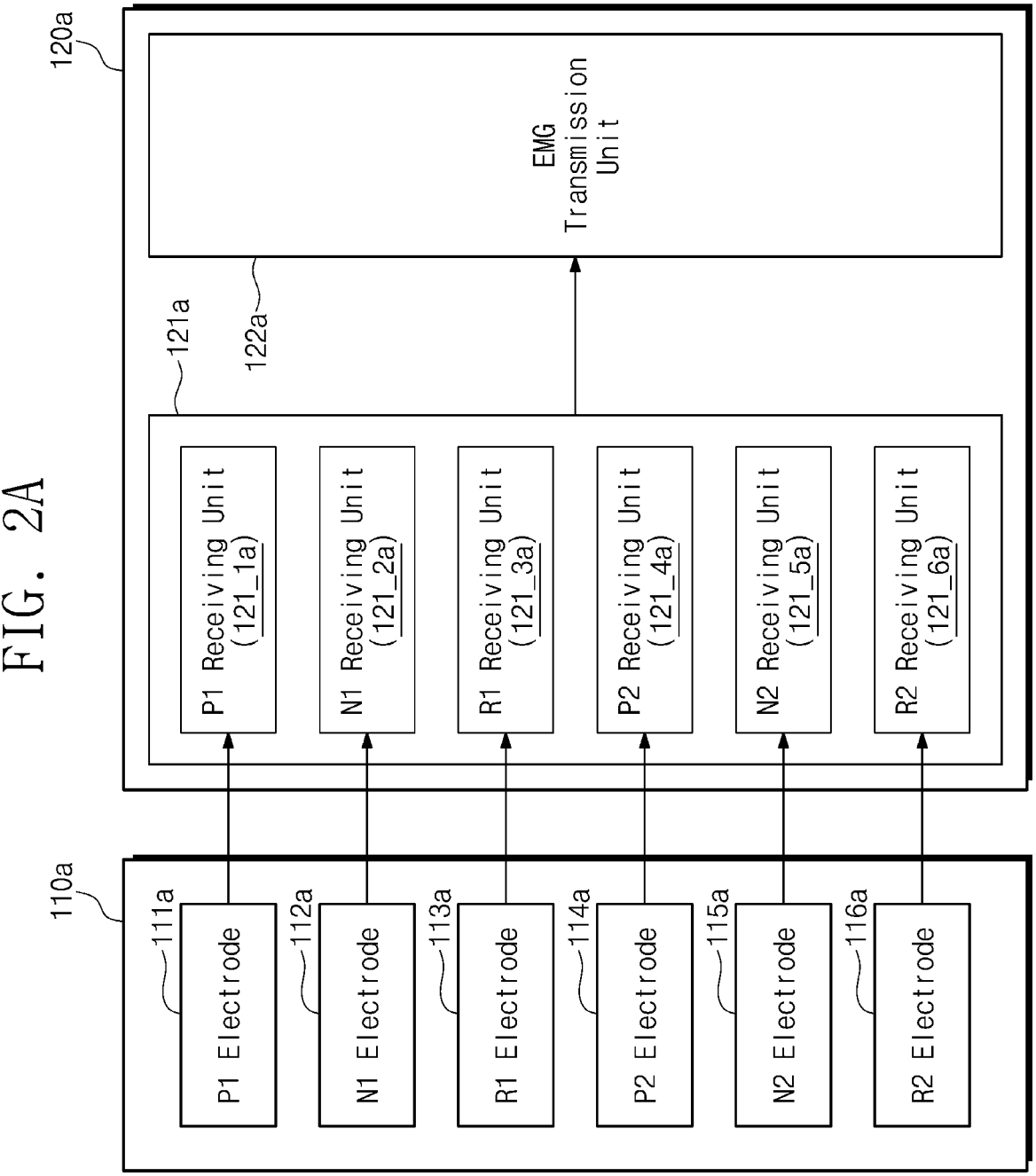
FIGS. 2A and 2B are block diagrams illustrating an EMG electrode unit and an EMG circuit unit of FIG. 1 in more detail.
Figure 2B:
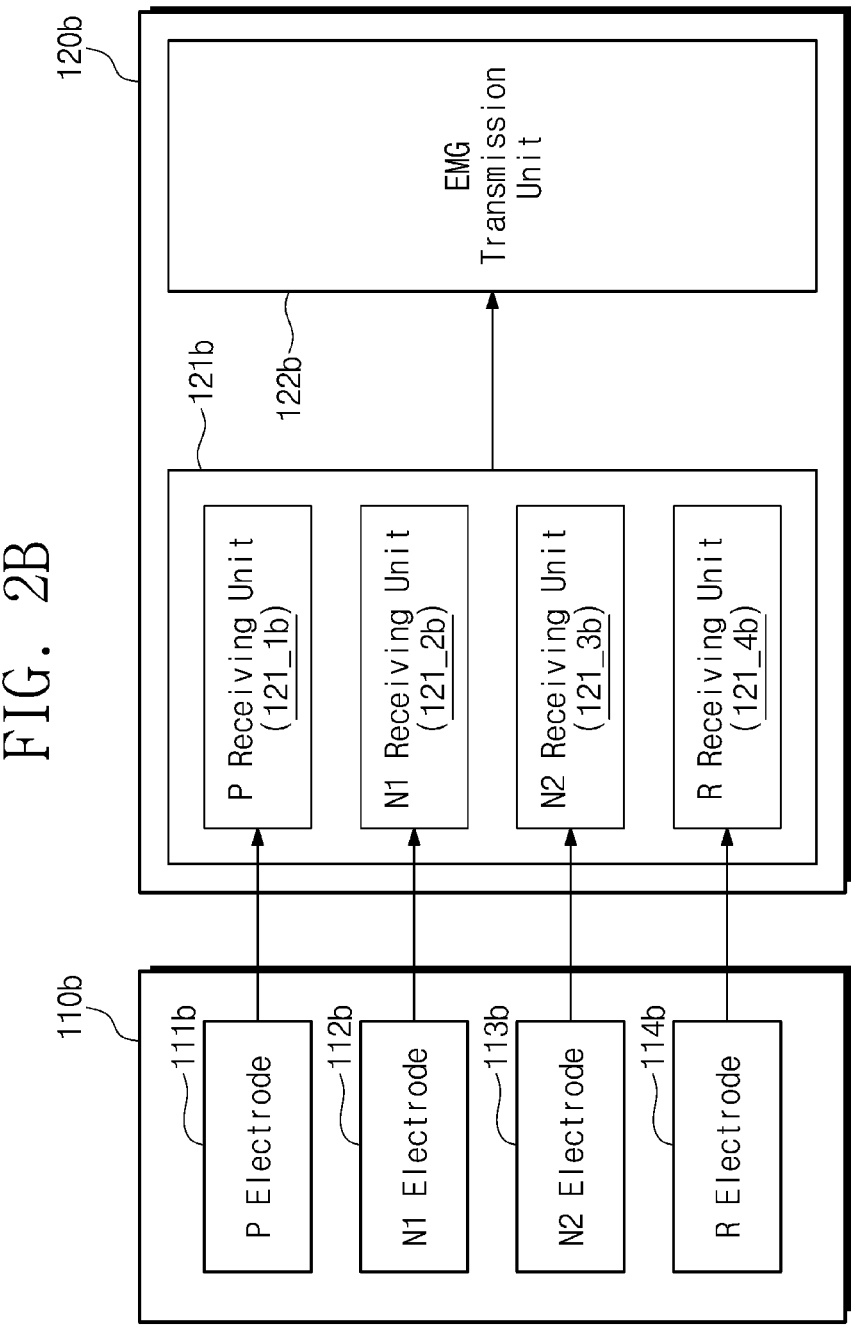

FIGS. 2A and 2B are block diagrams illustrating an EMG electrode unit and an EMG circuit unit of FIG. 1 in more detail. Referring to FIGS. 1 and 2A, an EMG electrode unit 110a may detect the EMG signal and may transmit the EMG signal to an EMG circuit unit 120a. The EMG electrode unit 110a may include a P1 electrode 111a, an N1 electrode 112a, an R1 electrode 113a, a P2 electrode 114a, an N2 electrode 115a, and an R2 electrode 116a. For example, the EMG electrode unit 110a may detect the EMG signal for one control target muscle through the plurality of electrodes 111a to 116a.

In an embodiment, the EMG electrode unit 110a may detect a P1 electrode signal through the P1 electrode 111a. The EMG electrode unit 110a may detect an N1 electrode signal through the N1 electrode 112a. The EMG electrode unit 110a may detect an R1 electrode signal through the R1 electrode 113a. The EMG electrode unit 110a may detect a P2 electrode signal through the P2 electrode 114a. The EMG electrode unit 110a may detect an N2 electrode signal through the N2 electrode 115a. The EMG electrode unit 110a may detect an R2 electrode signal through the R2 electrode 116a.

The EMG electrode unit 110a may transmit the EMG electrode signal to the EMG circuit unit 120a. For example, the EMG electrode unit 110a may transmit the P1 electrode signal, the N1 electrode signal, the R1 electrode signal, the P2 electrode signal, the N2 electrode signal, and the R2 electrode signal to the EMG circuit unit 120a.

The EMG circuit unit 120a may receive the EMG electrode signal from the EMG electrode unit 110a, convert it to digital data, and transmit the EMG channel data to the control unit 130. The EMG circuit unit 120a may include an EMG acquisition unit 121a and an EMG transmission unit 122a.

The EMG acquisition unit 121a may include a P1 receiving unit 121_1a, an N1 receiving unit 121_2a, an R1 receiving unit 121_3a, a P2 receiving unit 121_4a, an N2 receiving unit 121_5a, and an R2 receiving unit 121_6a. The P1 receiving unit 121_1a may receive the P1 electrode signal. The N1 receiving unit 121_2a may receive the N1 electrode signal. The R1 receiving unit 121_3a may receive the R1 electrode signal. Each of the remaining receiving units 121_4a to 121_6a may receive each of the corresponding electrode signals similarly, and detailed descriptions are omitted.

The EMG acquisition unit 121a may convert the received analog signal into the digital data. For example, the EMG acquisition unit 121a may convert an analog signal, which is a potential difference between the P1 electrode signal and the N1 electrode signal, based on the R1 electrode signal into digital data, that is, the first channel data. The EMG acquisition unit 121a may convert an analog signal, which is a potential difference between the P2 electrode signal and the N2 electrode signal, based on the received R2 electrode signal into digital data, that is, the second channel data. The EMG acquisition unit 121a may provide the first and second channel data to the EMG transmission unit 122a.

The EMG transmission unit 122a may receive the EMG channel data from the EMG acquisition unit 121a and may transmit it to the control unit 130. For example, the EMG channel data may include the first and second channel data.

As described above, the muscle control device 100 may detect the first and second channel data for one control target muscle. The first channel data may be detected through the P1 electrode 111a, the N1 electrode 112a, and the R1 electrode 113a. The second channel data may be detected through the P2 electrode 114a, the N2 electrode 115a, and the R2 electrode 116a.

Referring to FIGS. 1 and 2B, an EMG electrode unit 110b may detect the EMG signal and transmit it to an EMG circuit unit 120b. The EMG electrode unit 110b may include a P electrode 111b, an N1 electrode 112b, an N2 electrode 113b, and an R electrode 114b. For example, the EMG electrode unit 110b may detect the EMG signal for one control target muscle through the plurality of electrodes 111b to 114b.

In an embodiment, the EMG electrode unit 110b may detect a P electrode signal through the P electrode 111b. The EMG electrode unit 110b may detect the N1 electrode signal through the N1 electrode 112b. The EMG electrode unit 110b may detect the N2 electrode signal through the N2 electrode 113b. The EMG electrode unit 110b may detect an R electrode signal through the R electrode 114b.

The EMG electrode unit 110b may transmit the EMG electrode signal to the EMG circuit unit 120b. For example, the EMG electrode unit 110b may transmit the P electrode signal, the N1 electrode signal, the N2 electrode signal, and the R electrode signal to the EMG circuit unit 120b.

The EMG circuit unit 120b may receive the EMG electrode signal from the EMG electrode unit 110b, convert it to digital data, and transmit the EMG channel data to the control unit 130. The EMG circuit unit 120b may include an EMG acquisition unit 121b and an EMG transmission unit 122b.

The EMG acquisition unit 121b may include a P receiving unit 121_1b, an N1 receiving unit 121_2b, an N2 receiving unit 121_3b, and an R receiving unit 121_4b. The P receiving unit 121_1b may receive the P electrode signal sensed through the P electrode 111b. The N1 receiving unit 121_2b may receive the N1 electrode signal sensed through the N1 electrode 112b. The N2 receiving unit 121_3b may receive an N2 electrode signal sensed through the N2 electrode 113b. The R receiving unit 121_4b may receive the R electrode signal sensed through the R electrode 114b.

The EMG acquisition unit 121b may convert the received analog signal into digital data. For example, the EMG acquisition unit 121b may convert an analog signal, which is a potential difference between the P electrode signal and the N1 electrode signal, based on the R electrode signal, into digital data, that is, first channel data. The EMG acquisition unit 121b may convert an analog signal, which is a potential difference between the P electrode signal and the N2 electrode signal, based on the received R electrode signal into digital data, that is, second channel data. The EMG acquisition unit 121b may provide the first and second channel data to the EMG transmission unit 122b.

The EMG transmission unit 122b may receive the EMG channel data from the EMG acquisition unit 121b and may transmit it to the control unit 130. For example, the EMG channel data may include the first and second channel data.

As described above, the muscle control device 100 may detect the first and second channel data for one control target muscle. The first channel data may be detected through the P electrode 111b, the N1 electrode 112b, and the R electrode 114b. The second channel data may be detected through the P electrode 111b, the N2 electrode 113b, and the R electrode 114b.

Comparing FIGS. 2A and 2B, the EMG electrode unit 110a of FIG. 2A may sense the channel data through the P1 electrode 111a, the N1 electrode 112a, the R1 electrode 113a, the P2 electrode 114a, the N2 electrode 115a, and the R2 electrode 116a. The EMG electrode unit 110a may sense the first channel data through the P1 electrode 111a, the N1 electrode 112a, and the R1 electrode 113a, and may sense the second channel data through the P2 electrode 114a, the N2 electrode 115a, and the R2 electrode 116a. That is, the EMG electrode unit 110a may sense two channel data through six electrodes.

The EMG electrode unit 110b of FIG. 2B may share the P electrode and the R electrode. The EMG electrode unit 110b of FIG. 2B may sense the first channel data through the P electrode 111b, the N1 electrode 112b, and the R electrode 114b. The EMG electrode unit 110 may sense the second channel data through the P electrode 111b, the N2 electrode 113b, and the R electrode 114b. That is, the EMG electrode unit 110b may sense two channel data through four electrodes.

The muscle control device may reduce the number of electrodes used in the EMG electrode unit 110 by sharing the P electrode and the R electrode. As a result, a complexity of the muscle control device 100 may be reduced, and a size of the muscle to be controlled may be reduced. For example, the muscle control device 100 may control small muscles.

Figure 3:
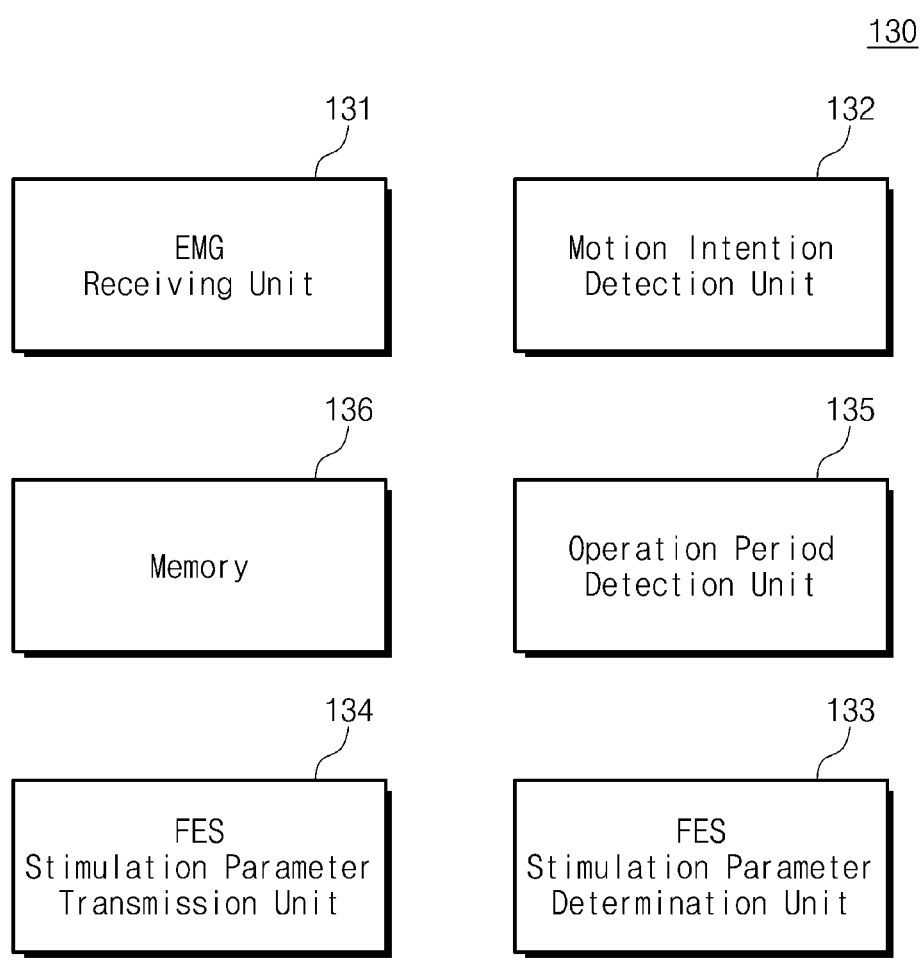
FIG. 3 is a block diagram illustrating a control unit of FIG. 1 in more detail.

FIG. 3 is a block diagram illustrating a control unit of FIG. 1 in more detail. Referring to FIGS. 1 and 3, the control unit 130 may include an EMG receiving unit 131, a motion intention detection unit 132, an FES stimulation parameter determination unit 133, the FES stimulation parameter transmission unit 134, an operation period detection unit 135, and a memory 136.

The EMG receiving unit 131 may receive the EMG channel data from the EMG circuit unit 120 and store or manage the EMG channel data. For example, the EMG receiving unit 131 may receive data for each channel and store or manage data for each channel. The EMG receiving unit 131 may receive the first and second channel data from the EMG circuit unit 120. The EMG receiving unit 131 may store or manage the first and second channel data in the memory 136. The EMG receiving unit 131 may provide the channel data to the motion intention detection unit 132.

In an embodiment, the EMG receiving unit 131 may communicate with the EMG circuit unit 120, based on various communication protocols such as the universal asynchronous receiver-transmitter (UART), the serial peripheral interface (SPI), the inter-integrated circuit (I2C), the Bluetooth, the universal serial bus (USB), the WiFi, etc.

The motion intention detection unit 132 may detect the motion intention, based on the EMG signal. In an embodiment, the motion intention detection unit 132 may extract the volitional electromyography (vEMG) signal or the vEMG data by performing a signal processing operation, based on the EMG channel data, and may operate the root mean square (RMS) of the vEMG.

When measuring the EMG signal, due to the application of the FES, a stimulation artifact and an M-wave may occur. For this reason, the EMG channel data may be distorted data. That is, the EMG channel data may be data in which the vEMG signal, the stimulation artifact, and the M-wave are combined. The stimulation artifact may be the FES signal itself, and the M-wave may be the electromyography signal induced by the FES. The vEMG signal may be the EMG signal reflecting the user's motion intention.

In an embodiment, the motion intention detection unit 132 may receive the EMG channel data from the EMG receiving unit 131. The motion intention detection unit 132 may extract the vEMG signal or the vEMG data which are obtained by removing effects of the stimulation artifact and the M-wave from the EMG channel data. The motion intention detection unit 132 may generate the EMG effective value by performing an operation based on the vEMG data. The motion intention detection unit 132 may provide the EMG effective value to the FES stimulation parameter determination unit 133.

The FES stimulation parameter determination unit 133 may determine the FES stimulation parameters, based on the volitional electromyography signal or the EMG effective value provided from the motion intention detection unit 132. For example, the FES stimulation parameter may be an element or variable that controls the electrical stimulation or the electrical signal output from the FES electrode unit 150. The FES stimulation parameters may be a combination of a pulse shape (mono-phasic or bi-phasic), an amplitude (or pulse size), a frequency, a period, a pulse width, a hold time, a waveform, etc. The FES stimulation parameters may be used to control the intensity of electrical stimulation or electrical energy transferred to the neuromuscular, and to determine a muscle contractility.

In an embodiment, since the EMG effective value (RMS) indicates the user's motion intention, the FES stimulation parameter determination unit 133 may determine the values of the FES stimulation parameters to match the user's motion intention, based on the EMG effective value (RMS). That is, the FES stimulation parameter determination unit 133 may determine the values of the stimulation parameters such that electrical energy corresponding to the user's motion intention is transferred to the neuromuscular.

In an embodiment, the FES stimulation parameter determination unit 133 may receive the EMG effective value (RMS) from the motion intention detection unit 132. The EMG effective value (RMS) may indicate the user's motion intention. For example, when the EMG effective value (RMS) is large, it may indicate an intention of the user to move the joint by applying a lot of force. When the EMG effective value (RMS) is small, it may indicate an intention of the user to move the joint by applying a small force.

The FES stimulation parameter determination unit 133 may adjust stimulation parameter values such that the FES is provided to the neuromuscular in accordance with the user's motion intention. For example, when the EMG effective value (RMS) is large, the FES stimulation parameter determination unit 133 may adjust the stimulation parameters such that electrical energy transferred to the neuromuscular increases. Alternatively, the FES stimulation parameter determination unit 133 may adjust the stimulation parameters such that large electrical energy is transferred to the neuromuscular. When the EMG effective value (RMS) is small, the FES stimulation parameter determination unit 133 may adjust the stimulation parameters such that electrical energy transferred to the neuromuscular decreases. Alternatively, the FES stimulation parameter determination unit 133 may adjust the stimulation parameters such that less electrical energy is transferred to the neuromuscular.

In an embodiment, the FES stimulation parameter determination unit 133 may determine the values of stimulation parameters in proportion to the EMG effective value (RMS). For example, the FES stimulation parameter determination unit 133 may adjust the pulse size or the pulse amplitude, based on the EMG effective value (RMS). The pulse amplitude may be proportional to the EMG effective value (RMS). As the EMG effective value (RMS) increases, the pulse amplitude may increase, and as the EMG effective value (RMS) decreases, the pulse amplitude may decrease. The FES stimulation parameter determination unit 133 may generate a pulse amplitude value by performing a multiplication operation on the EMG effective value (RMS) and a predetermined value.

In an embodiment, the FES stimulation parameter determination unit 133 may determine values of the stimulation parameters contrary to the movement direction by using the EMG effective values (RMS) of an agonist muscle and an antagonist muscle. For example, the FES stimulation parameter determination unit 133 may improve an exercise effect of the user by adjusting the FES stimulation parameters such that the muscle is controlled contrary to the user's motion intention (i.e., to contract the antagonist muscle in proportion to the vEMG effective value of the agonist muscle), thereby generating a load on the control target muscle.

The FES stimulation parameter transmission unit 134 may transmit the stimulation parameters provided from the FES stimulation parameter determination unit 133 to the FES circuit unit 140. In an embodiment, the FES stimulation parameter transmission unit 134 may communicate with the FES circuit unit 140, based on various communication protocols such as the universal asynchronous receiver-transmitter (UART), the serial peripheral interface (SPI), the inter-integrated circuit (I2C), the Bluetooth, the universal serial bus (USB), the WiFi, etc.

The control unit 130 may further include the operation period detection unit 135. The operation period detection unit 135 may receive the EMG channel data from the EMG receiving unit 131. The operation period detection unit 135 may determine an operation period, based on the EMG channel data. Alternatively, the operation period detection unit 135 may determine whether the user is currently performing a periodic operation, based on the EMG channel data. For example, the periodic motion may include walking, running, etc.

In an embodiment, when it is determined that a periodic operation is currently being performed, the operation period detection unit 135 may adjust or control an FES time. For example, the operation period detection unit 135 may make the FES time equal to an EMG signal time. Alternatively, the operation period detection unit 135 may make the FES time different from the EMG signal time. A more detailed description of this will be described in FIG. 8.

The memory 136 may include various types of volatile or nonvolatile storage media. For example, the memory may include a ROM and a RAM. The memory 136 may store the EMG channel data provided from the EMG circuit unit 120.

Figure 4:
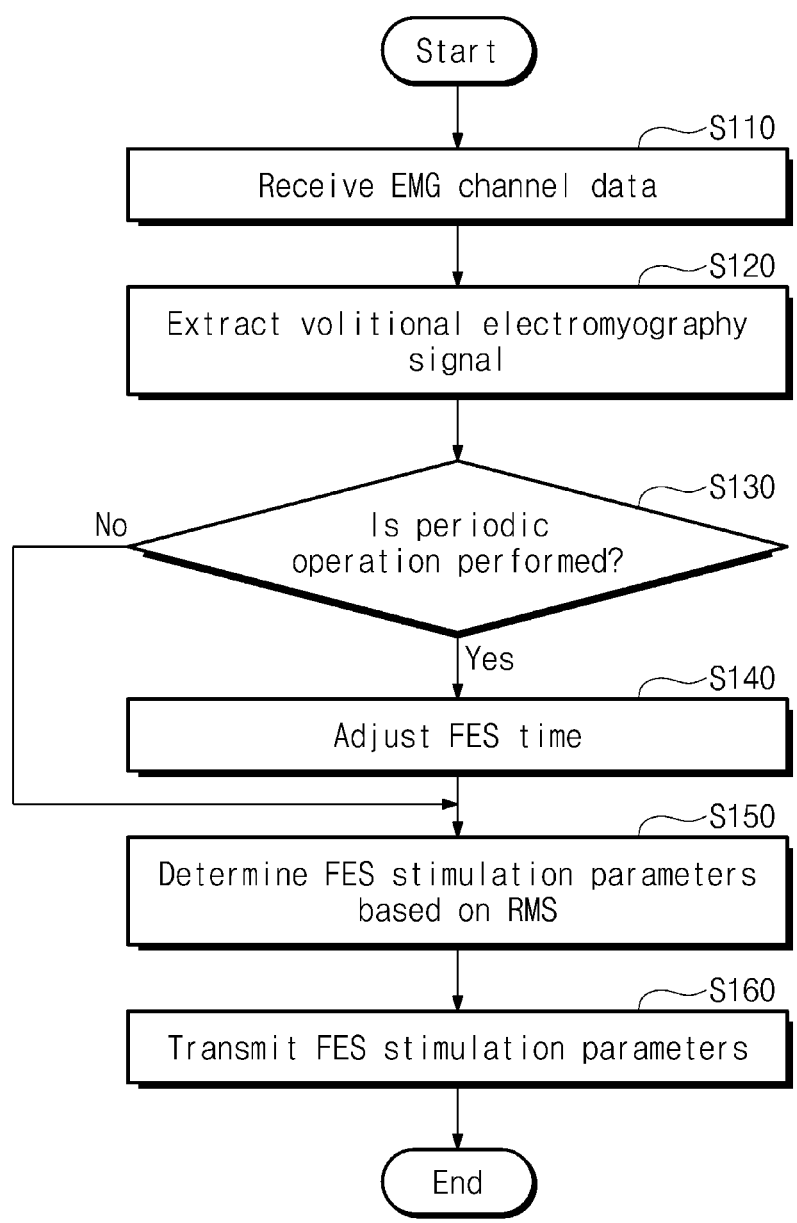
FIG. 4 is a flowchart illustrating an operation method of a control unit of FIG. 1.

FIG. 4 is a flowchart illustrating an operation method of a control unit of FIG. 1. Referring to FIGS. 1, 3, and 4, in operation S110, the control unit 130 may receive the EMG channel data. For example, the control unit 130 may receive the first and second channel data from the EMG circuit unit 120.

In operation S120, the control unit 130 may extract the volitional electromyography signal from the EMG channel data. For example, due to the FES application during EMG measurement, the EMG channel data may be data in which the vEMG signal, the stimulation artifact, and the M-wave are combined. The control unit 130 may extract the vEMG signal or the vEMG data which are obtained by removing the influence of the stimulation artifact and the M-wave to identify the motion intention. The control unit 130 may generate the EMG effective value (RMS) by performing an operation based on the vEMG data.

In operation S130, the control unit 130 may determine whether the user is performing a periodic operation. For example, the control unit 130 may determine whether the user wearing the muscle control device 100 is performing a walking motion. When it is determined that the periodic operation is being performed, the control unit 130 proceeds to operation S140. When it is determined that the periodic operation is not performed, the control unit 130 proceeds to operation S150.

In operation S140, the control unit 130 may adjust the FES time. The control unit 130 may allow the FES time to be the same as the EMG time. Alternatively, the control unit 130 may control the FES time differently from the EMG time. For example, the control unit 130 may control the FES time to precede the EMG time. That is, the control unit 130 may assist the user by transferring the FES prior to the user's motion intention. The control unit 130 may allow the FES time to be later than the EMG time. That is, the control unit 130 may assist the user by transferring the FES later than the user's motion intention.

In operation S150, the control unit 130 may determine the FES stimulation parameters, based on the RMS. The control unit 130 may determine values of FES stimulation parameters based on the RMS. For example, the control unit 130 may adjust the FES stimulation parameters such that as the RMS increases, the FES intensity or FES electrical energy increases. That is, the values of the FES stimulation parameters may be proportional to the EMG effective value (RMS). The control unit 130 may identify the user's motion intention in real time, and allow the FES in accordance with the motion intention to be transferred.

In operation S160, the control unit 130 may transmit the FES stimulation parameters to the FES circuit unit 140. As described above, the control unit 130 may detect the EMG signal to identify the user's motion intention, and may determine the FES stimulation parameters such that the FES intensity or the FES electrical energy corresponding to the user's motion intention is transferred to the neuromuscular. The control unit 130 may adjust the FES time before/after the user's motion intention with respect to the periodic operation.

Figure 5:
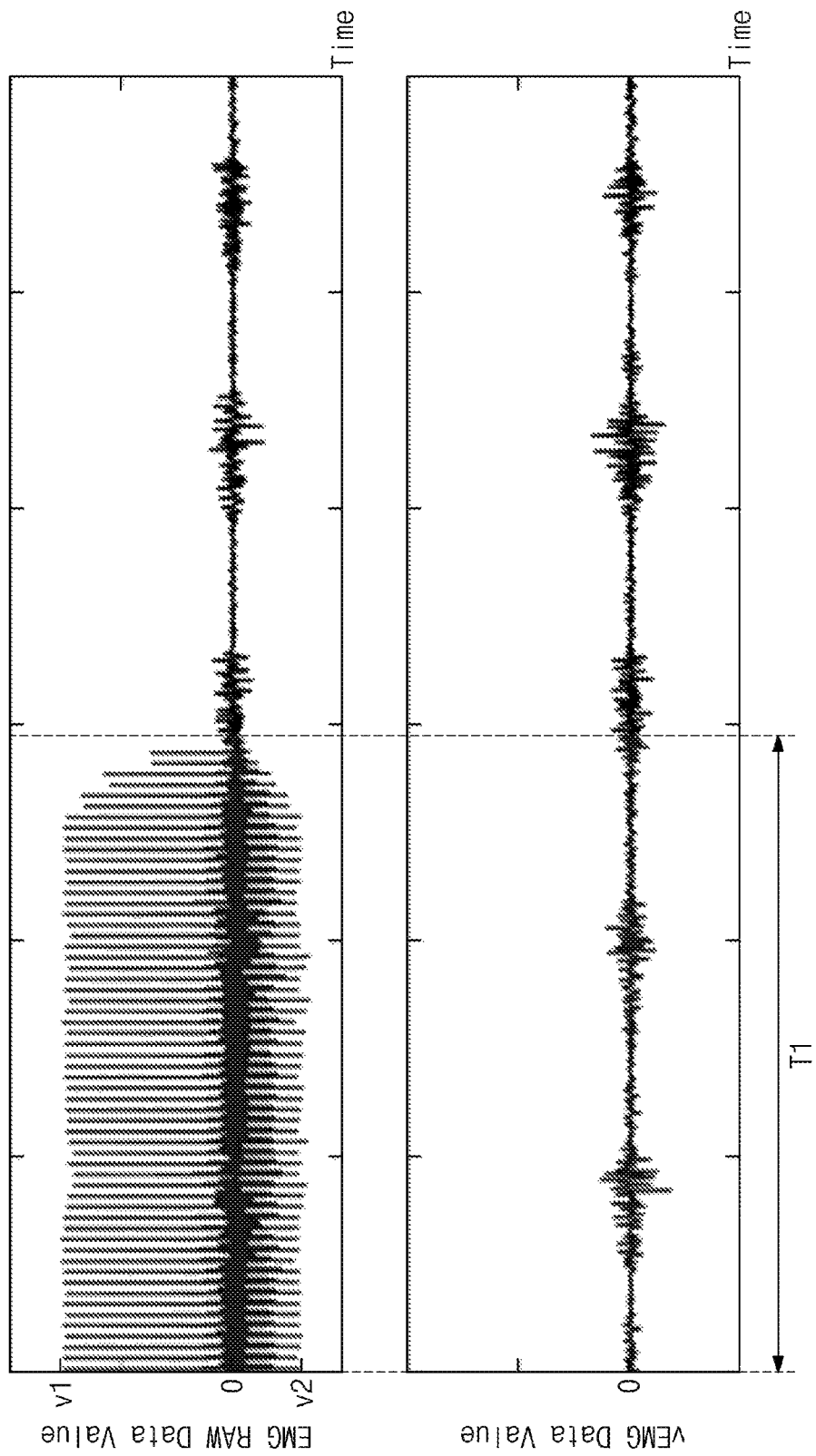
FIG. 5 are graphs describing EMG RAW data and vEMG data by way of example.

FIG. 5 are graphs describing EMG RAW data and vEMG data by way of example. Referring to FIGS. 1, 3, and 5, the motion intention detection unit 132 may receive the EMG channel data from the EMG receiving unit 131. The motion intention detection unit 132 may extract the vEMG data by performing a signal processing operation on the EMG channel data. The EMG channel data may be EMG RAW data. That is, the EMG channel data may be data in which the volitional electromyography signal, the stimulation artifact, and the M-wave are combined. The motion intention detection unit 132 may perform a signal processing operation to extract the vEMG data, which are the EMG channel data which are obtained by removing effects of the stimulation artifact and the M-wave.

In an embodiment, the motion intention detection unit 132 may obtain or calculate an FES period. The motion intention detection unit 132 may extract period data from the EMG channel data, based on the FES period. The motion intention detection unit 132 may extract the vEMG data by performing a difference calculation on period data acquired during a plurality of periods.

For example, the motion intention detection unit 132 may receive the first and second channel data. During the first period, the motion intention detection unit 132 may generate or extract first channel previous period data and second channel previous period data. During the second period after the first period, the motion intention detection unit 132 may generate or extract first channel current period data and the second channel current period data. The motion intention detection unit 132 may generate first channel difference calculation data by performing the difference calculation on the first channel previous period data and the first channel current period data. The motion intention detection unit 132 may generate second channel difference calculation data by performing the difference calculation on the second channel current period data and the second channel previous period data.

The motion intention detection unit 132 may extract the vEMG data by performing a difference operation on the first channel difference calculation data and the second channel difference calculation data. That is, the motion intention detection unit 132 may extract vEMG data, which are EMG channel data which are obtained by removing the effects of the stimulation artifact and the M-wave.

The motion intention detection unit 132 may generate the effective value (RMS) of the EMG signal by performing the root mean square operation on the extracted EMG channel data.

Horizontal axes of the graphs of FIG. 5 indicate a time, and a vertical axis indicates the EMG RAW data value, and the vEMG data value. The illustrated graphs are for explaining effects according to an embodiment of the present disclosure, and the scope of the present disclosure is not limited thereto.

During a first time T1, it may be confirmed that the EMG RAW data value is a combination of a signal that vibrates greatly from the first value v1 to the second value v2, that is a signal with a large amplitude, and a signal with a small amplitude converged to '0'. On the other hand, during the first time T1, only a signal having a small amplitude converged to '0' may be identified as the vEMG data value. That is, referring to the graphs of FIG. 5, it may be confirmed that not only the vEMG signal but also the stimulation artifact and the M-wave are combined in the EMG channel data.

Figure 6:
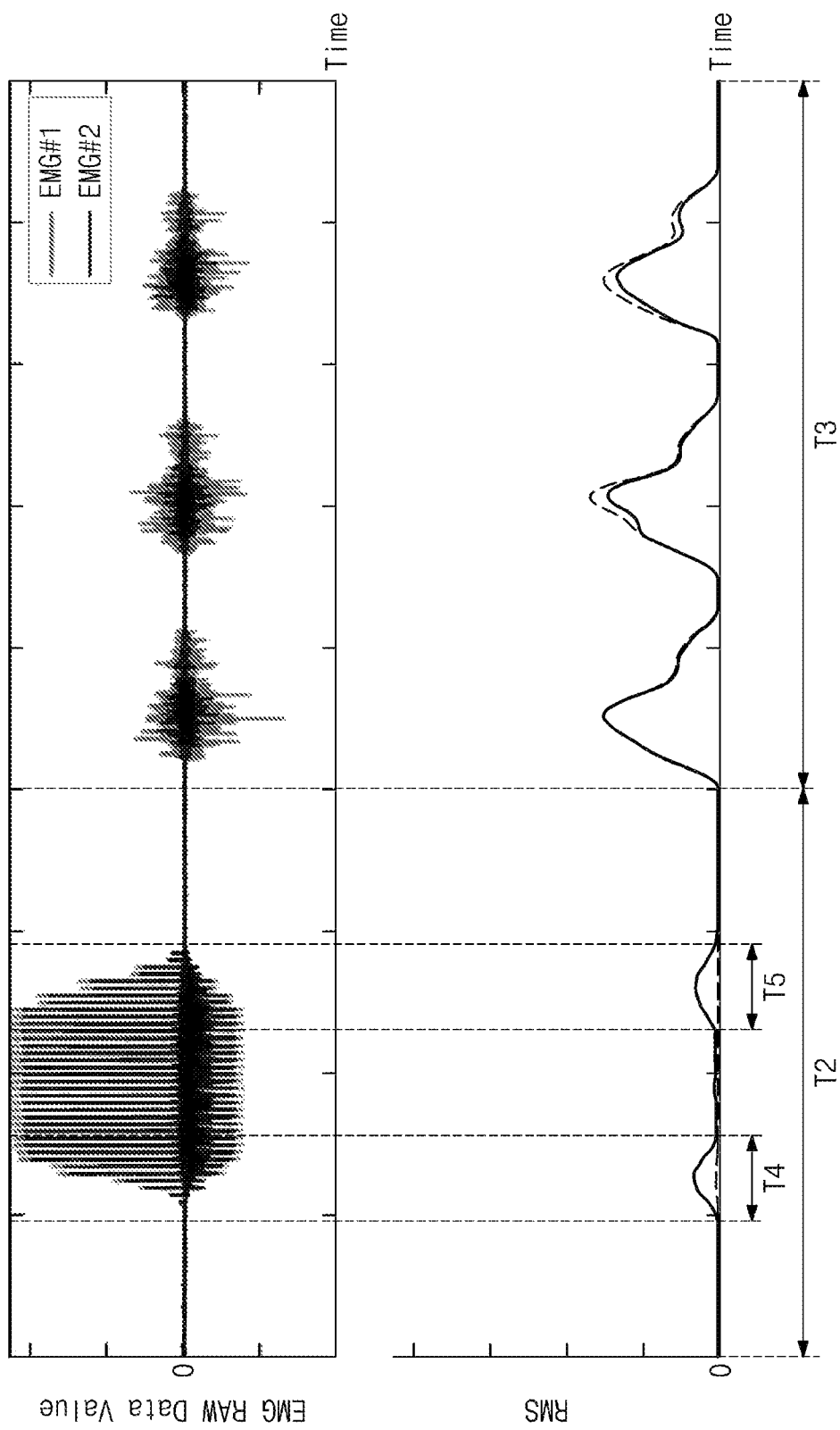
FIG. 6 are graphs illustrating a signal processing effect of a motion intention detection unit of FIG. 3.

FIG. 6 are graphs illustrating a signal processing effect of a motion intention detection unit of FIG. 3. Referring to FIGS. 1, 3, and 6, horizontal axes of the graphs indicate a time, and vertical axes indicate the EMG RAW data values, and the EMG effective value (RMS).

The graphs of FIG. 6 indicate results of measuring the EMG signal when the user wearing the muscle control device 100 does not apply force to the muscle and only applies FES during a second time T2. The graphs of FIG. 6 indicate results of measuring the EMG signal when the user applies force to the muscle and applies FES during a third time period T3.

The dashed-dotted line illustrates the EMG effective value subjected to signal processing by a method according to an embodiment of the present disclosure. The solid line illustrates the EMG effective value subjected to signal processing by a general method (e.g., a Compiler method, a difference calculation between the data of the current FES pulse period and the data of the previous period from the EMG data of one channel, etc.).

During the second time, the dashed-dotted line remains at '0'. On the other hand, it may be seen that the solid line has a value of '0' or more during the fourth and fifth times T4 and T5, which are the periods in which the FES stimulation changes. That is, when the signal is processed by the method according to the embodiment of the present disclosure, the effect of the stimulation artifact is removed, but when the signal is processed by the general method, it may be confirmed that the EMG effective value is not '0' due to the influence of the stimulation artifact.

That is, the motion intention detection unit 132 according to an embodiment of the present disclosure may perform signal processing to extract the vEMG data which are obtained by removing effects of the stimulation artifact and the M-wave. Accordingly, the control unit 130 may accurately identify the user's motion intention.

Figure 7:
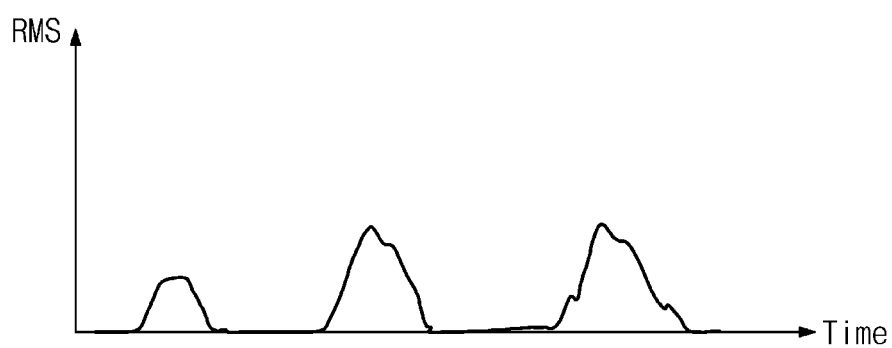
FIG. 7 are graphs illustrating a relationship between an EMG effective value and an FES output.
Figure 7:
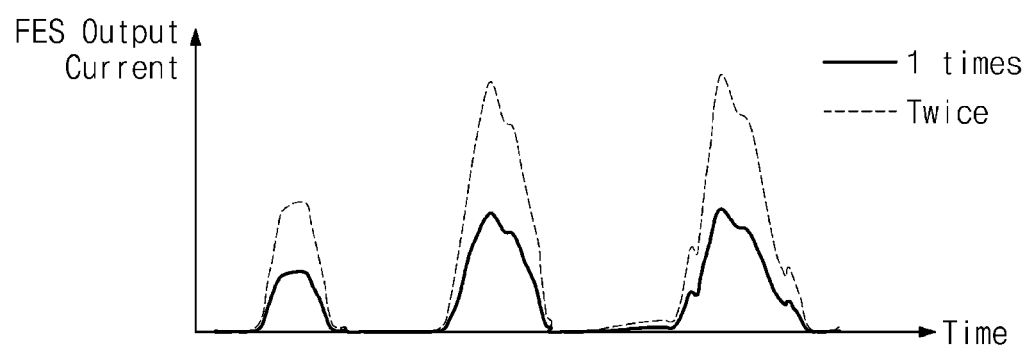

FIG. 7 are graphs illustrating a relationship between an EMG effective value and an FES output. Referring to FIGS. 1, 3, and 7, horizontal axes of the graphs indicate a time, and vertical axes indicate the EMG effective value (RMS), and an FES output current. The current of the FES output signal multiplied by the EMG effective value (RMS) is illustrated by a solid line, and the current of the FES output signal doubled by the EMG effective value (RMS) is illustrated by a dashed-dotted line. The illustrated graphs are merely for explaining effects according to embodiments of the present disclosure, and the scope of the present disclosure is not limited thereto.

In an embodiment, the FES stimulation parameter determination unit 133 may determine values of the stimulation parameters in proportion to the EMG effective value (RMS). For example, when the EMG effective value (RMS) is large, it indicates that the user wearing the muscle control device 100 applies a lot of force to move the joint. When the EMG effective value (RMS) is small, it indicates that the user applies a small force to move the joint. Accordingly, when the EMG effective value (RMS) is large, the FES stimulation parameter determination unit 133 may adjust the stimulation parameters such that electrical energy transferred to the neuromuscular increases. When the EMG effective value (RMS) is small, the motion intention detection unit 132 may adjust stimulation parameters such that electrical energy transmitted to the neuromuscular decreases.

Accordingly, as the EMG effective value (RMS) increases, the current of the FES output signal may increase. That is, the current of the FES output signal may be proportional to the EMG effective value (RMS).

Figure 8:
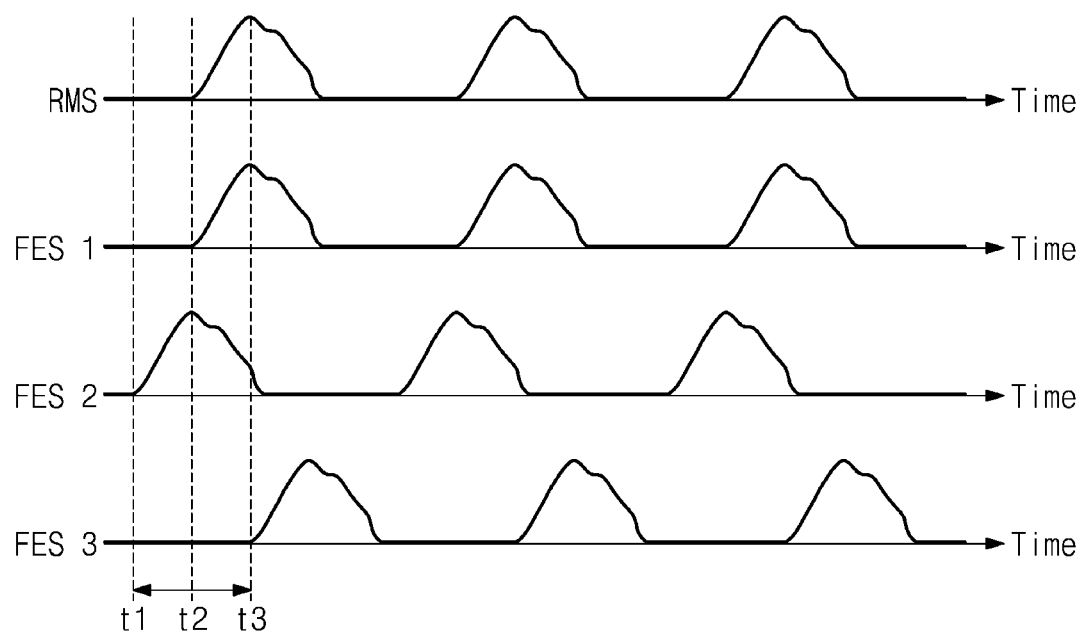
FIG. 8 are graphs illustrating a result of adjusting an FES time of an operation period detection unit 135 of FIG. 3.

FIG. 8 are graphs illustrating a result of adjusting an FES time of the operation period detection unit 135 of FIG. 3. Horizontal axes of the graphs of FIG. 8 indicate a time, and vertical axes indicate the EMG effective value (RMS), a first FES output current (FES1), a second FES output current (FES2), and a third FES output current (FES3). The illustrated graphs are for explaining effects according to an embodiment of the present disclosure, and the scope of the present disclosure is not limited thereto.

The first FES output current (FES1) illustrates the case where the EMG time and the FES time are the same, the second FES output current (FES2) illustrates the case where the FES time precedes the EMG time, and the third FES output current (FES3) illustrates the case where FES time is later than the time EMG.

Referring to FIGS. 1, 3, and 8, the operation period detection unit 135 may determine whether the user currently performs a periodic operation. The operation period detection unit 135 may receive the EMG channel data from the EMG receiving unit 131 or may receive the EMG effective value (RMS) from the motion intention detection unit 132.

When it is determined that the user performs a periodic operation, the operation period detection unit 135 may control the EMG time and the FES time to be the same as illustrated in the FES1 in the graph of FIG. 8. For example, when the EMG effective value increases and then decreases from a second time point t2, the operation period detection unit 135 may control the first FES output current FES1 to increase and then decrease from the second time point t2.

The operation period detection unit 135 may control the FES time to precede the EMG time, as illustrated in the FES2 in the graph of FIG. 8. For example, when the EMG effective value increases and then decreases from the second time point t2, the operation period detection unit 135 may control the second FES output current FES2 to increase and then decrease from the first time point t1 that precedes the second time point t2.

The operation period detection unit 135 may control the FES time to be later than the EMG time, as illustrated in FES3 in the graph of FIG. 8. For example, when the EMG effective value increases and then decreases from the second time point t2, the operation period detection unit 135 may control the third FES output current FES3 to increase and then decrease from the third time point t3 that is later than the second time point t2.

The operation period detection unit 135 may provide time information to the FES stimulation parameter determination unit 133 to adjust the FES time. The FES stimulation parameter determination unit 133 may adjust the stimulation parameters, based on time information provided from the operation period detection unit 135.

When the FES time is adjusted to precede the EMG time, the muscle control device 100 may contract the muscle in advance prior to the motion intention. In this case, the user may psychologically feel that he/she is being further psychologically assisted by the muscle control device 100 in performing a periodic operation. The muscle control device 100 may control the muscle efficiently by adjusting the FES time.

To sense the timing of the operation, the muscle control device 100 may be used with a foot switch, an inertia measurement unit (IMU) sensor, or a goniometer. The muscle control device 100 may adjust the FES time, based on information acquired using the foot switch, the inertia measurement unit (IMU) sensor, or the goniometer. While the user performs a periodic motion (e.g., walking), the muscle control device 100 may derive a gait cycle by using the IMU sensor. The muscle control device 100 may control the muscle according to the period by using the EMG signal and the gait cycle together.

Figure 9:
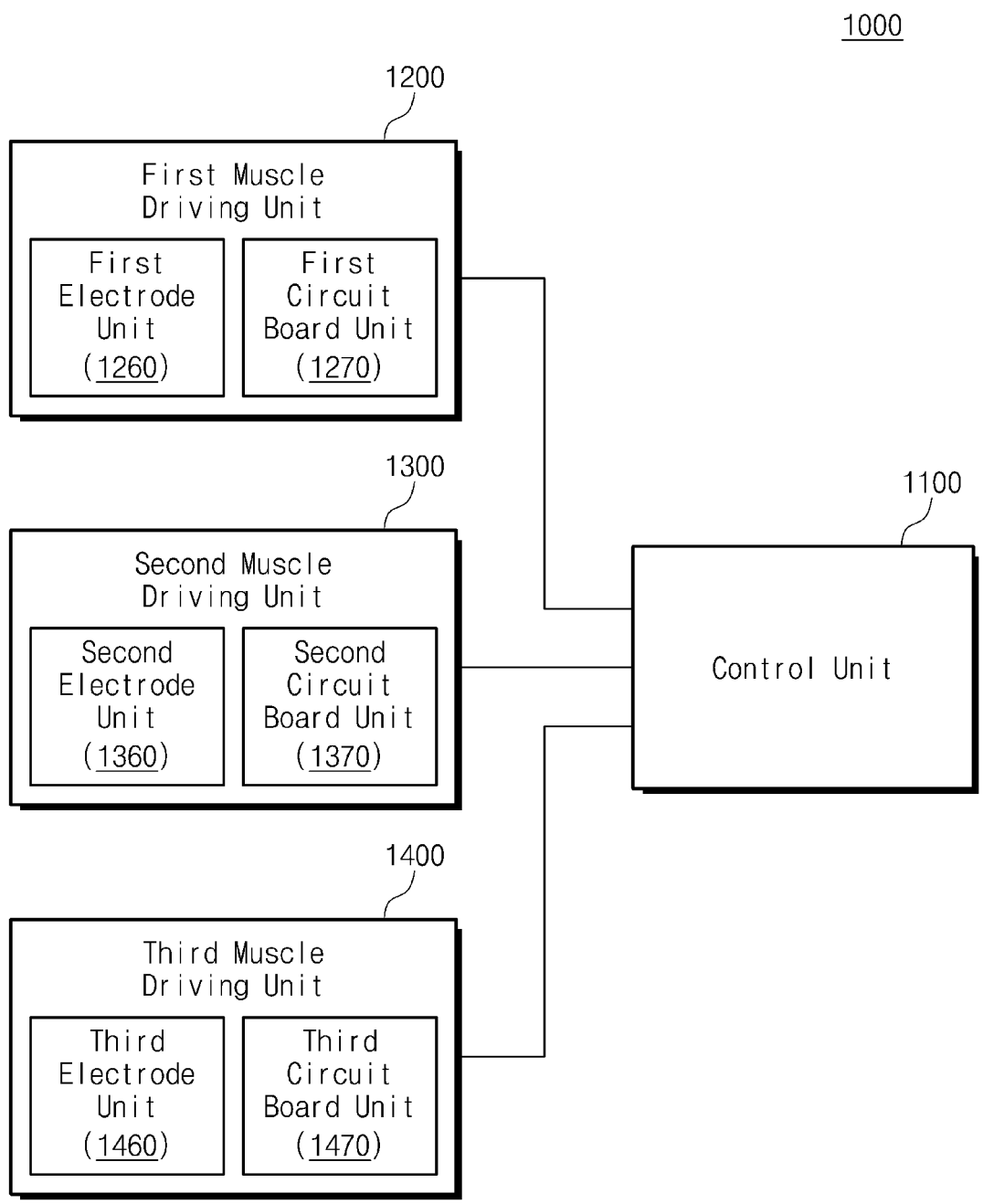
FIG. 9 is a block diagram illustrating a muscle control device 1000 according to an embodiment of the present disclosure.

FIG. 9 is a block diagram illustrating a muscle control device 1000 according to an embodiment of the present disclosure. Referring to FIGS. 1 and 9, the muscle control device 1000 may include a control unit 1100, a first muscle driving unit 1200, a second muscle driving unit 1300, and a third muscle driving unit 1400. The scope of the present disclosure is not limited thereto, and the number of muscle driving units and the number of control units may vary.

Unlike the control unit of FIG. 1, the control unit 1100 may manage or control a plurality of control target muscles. The control unit of FIG. 1 may receive the EMG channel data for one control target muscle and may adjust the stimulation parameters based on the EMG channel data. On the other hand, the control unit 1100 of FIG. 9 may receive the EMG channel data for a plurality of control target muscles and may adjust the stimulation parameters based on the EMG channel data.

The first muscle driving unit 1200 may include a first electrode unit 1260 and a first circuit board unit 1270. The first electrode unit 1260 may include an EMG electrode unit and an FES electrode unit, like the electrode unit described above. The first circuit board unit 1270 may include an EMG circuit unit and an FES circuit unit, like the circuit board unit described above. The first muscle driving unit 1200 may sense the EMG signal for a first muscle and may transfer the FES to the first muscle.

The second muscle driving unit 1300 may include a second electrode unit 1360 and a second circuit board unit 1370. The second electrode unit 1360 may include an EMG electrode unit and an FES electrode unit, like the electrode unit described above. The second circuit board unit 1370 may include an EMG circuit unit and an FES circuit unit, like the circuit board unit described above. The second muscle driving unit 1300 may sense the EMG signal for a second muscle and may transfer the FES to the second muscle. The second muscle may be a control target muscle different from the first muscle.

The third muscle driving unit 1400 may include a third electrode unit 1460 and a third circuit board unit 1470. The third electrode unit 1460 may include an EMG electrode unit and an FES electrode unit, like the electrode unit described above. The third circuit board unit 1470 may include an EMG circuit unit and an FES circuit unit, like the circuit board unit described above. The third muscle driving unit 1400 may sense the EMG signal for the third muscle and may transfer the FES to the third muscle. The third muscle may be a control target muscle different from the first and second muscles.

For example, the control unit 1100 may determine the FES stimulation parameters for the first muscle, based on the first and second channel data for the first muscle received from the first muscle driving unit 1200, and may transmit the FES stimulation parameters to the first muscle driving unit 1200. The control unit 1100 may determine the FES stimulation parameters for the second muscle, based on the first and second channel data for the second muscle received from the second muscle driving unit 1300, and may transmit the FES stimulation parameters to the second muscle driving unit 1300. The control unit 1100 may determine the FES stimulation parameters for the third muscle, based on the first and second channel data for the third muscle received from the third muscle driving unit 1400, and may transmit the FES stimulation parameters to the third muscle driving unit 1400.

As such, the control unit 1100 may receive channel data for each of the muscles, manage it for each muscle, and determine and transmit corresponding FES stimulation parameters based on channel data for each of the muscles. That is, the control unit 1100 may manage the EMG channel data for a plurality of control target muscles, and may determine the stimulation parameters for a plurality of control target muscles.

By way of example, in FIG. 9, although one control unit manages or controls three muscle driving units, the number of muscle driving units managed by the control unit may vary. The muscle control device may include a plurality of control units. For example, although not illustrated, the first and second muscle driving units may be managed by a first control unit, and the third muscle driving unit may be managed by a second control unit.

Figure 10:
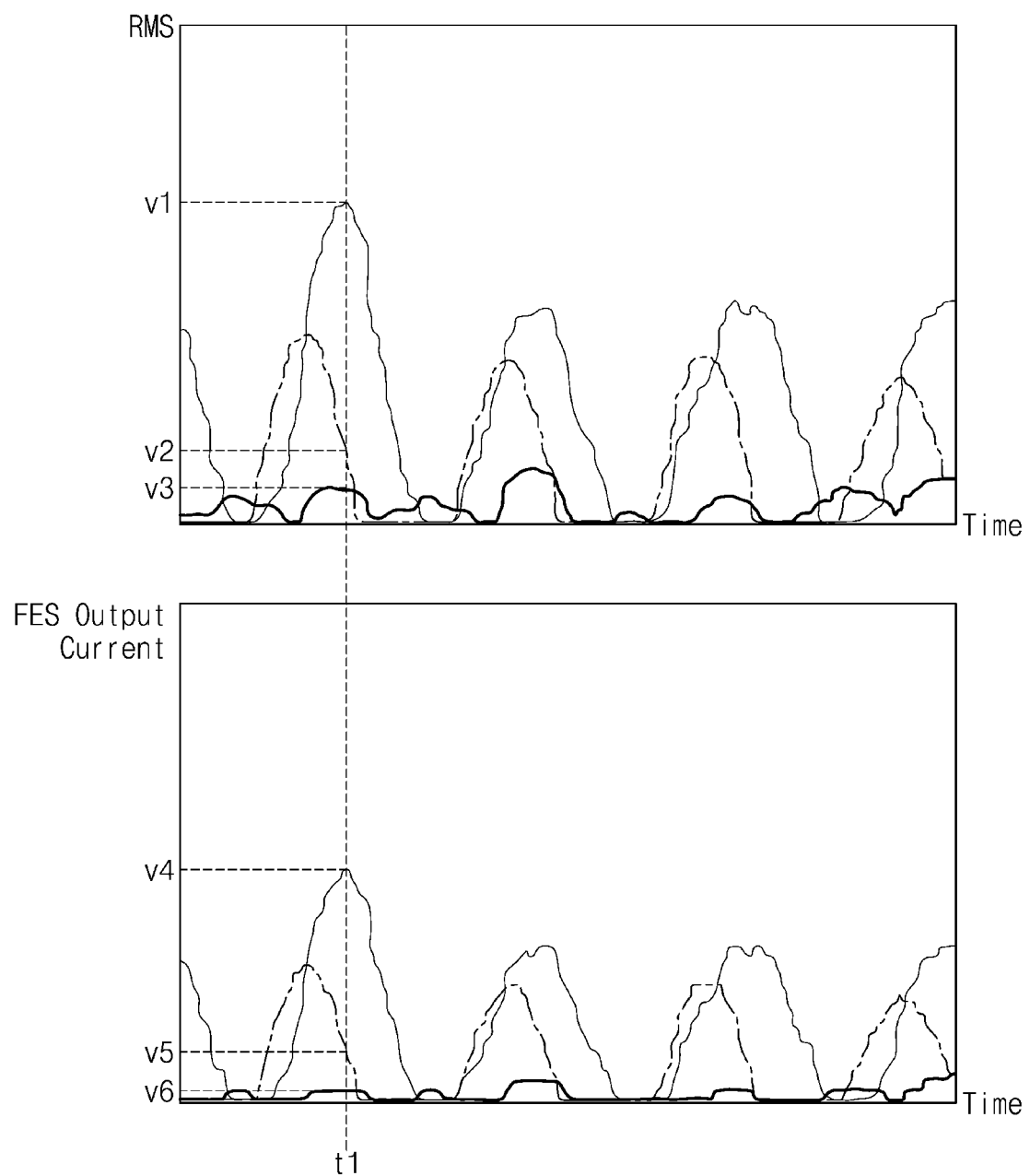
FIG. 10 are graphs illustrating an RMS and an FES for a plurality of control target muscles.

FIG. 10 are graphs illustrating an RMS and an FES for a plurality of control target muscles. Horizontal axes of the graphs of FIG. 10 indicate a time, and vertical axes indicate the EMG effective value (RMS), and the FES output current. The solid line is for the first muscle, the dashed line is for the second muscle, and the thick line is for the third muscle.

Referring to FIGS. 9 and 10, the muscle control device 1000 may control the plurality of control target muscles. The muscle control device 1000 may generate the EMG effective values (RMS) by detecting EMG signals for the first muscle, the second muscle, and the third muscle in real time. As illustrated in the graph of FIG. 10, the EMG effective values (RMS) may be different depending on the muscle. For example, a first value v1 may be the EMG effective value (RMS) for the first muscle at a first time point t1, and a second value v2 may be the EMG effective value (RMS) for the second muscle at the first time point t1, and a third value v3 may be the EMG effective value (RMS) for the third muscle at the first time point t1. The first value v1, the second value v2, and the third value v3 may be different from one another.

The muscle control device 1000 may determine the FES stimulation parameters of each of the muscles based on the EMG effective value of each of the muscles. The muscle control device 1000 may transfer different FESs to each of the muscles. For example, as illustrated in the graph of FIG. 10, at the first time point t1, a fourth value v4 may be an FES output current value transferred to the first muscle at the first time point t1, and a fifth value v5 may be an FES output current value transferred to the second muscle at the first time point t1, and a sixth value v6 may be an FES output current value transmitted to the third muscle at the first time point t1. The fourth value v4, the fifth value v5, and the sixth value v6 may be different from one another.

As described above, the muscle control device 1000 may independently control the plurality of control target muscles. Since the EMG effective values (RMS) of each of the plurality of muscles are different from one another at the same time point, the contraction timing and intensity required for each of the muscles may be different from each other. The muscle control device 1000 may independently control each of the muscles so as to meet the motion intention of each of the muscles. That is, the muscle control device 1000 may transfer FES corresponding to the motion intention to each of the plurality of muscles. Accordingly, the muscle control device 1000 may assist the user to perform a natural movement.

Figure 11:
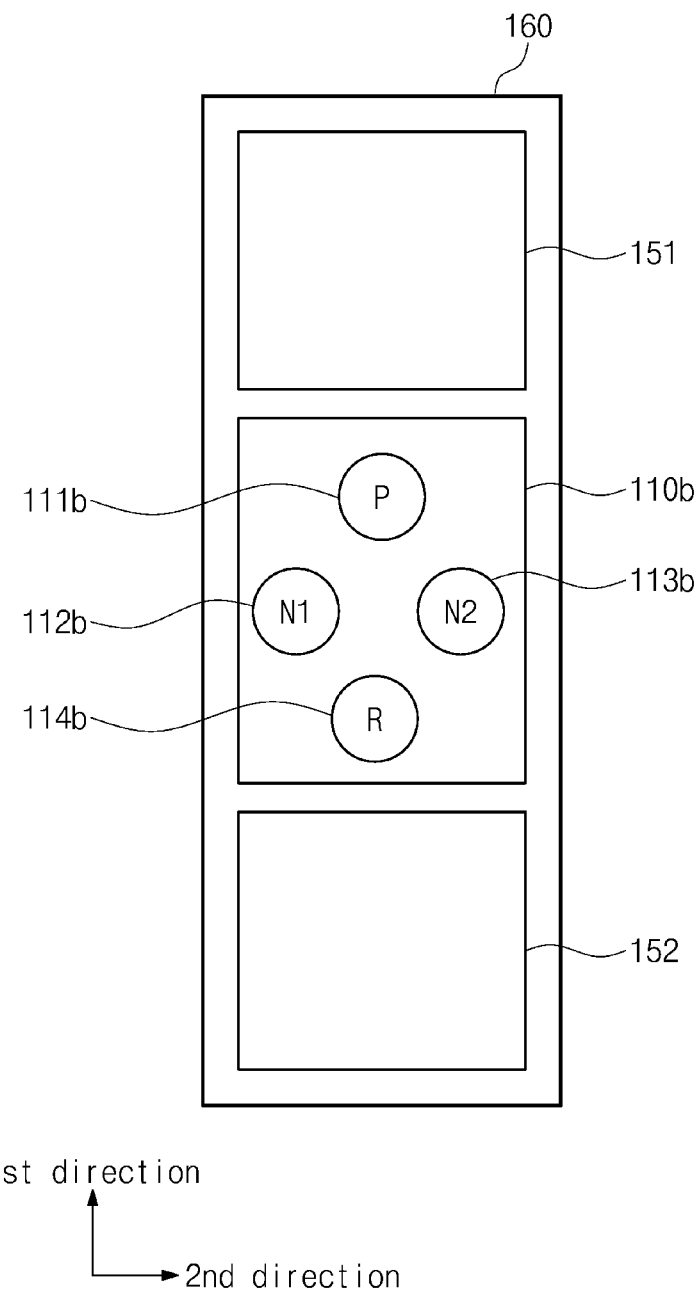
FIG. 11 is a diagram illustrating a physical arrangement of an electrode unit of FIG. 1.

FIG. 11 is a diagram illustrating a physical arrangement of an electrode unit of FIG. 1. Referring to FIGS. 1, 2B and 11, the electrode unit 160 may include the EMG electrode unit 110, the first FES electrode 151, and the second FES electrode 152. In FIG. 11, it is assumed that the EMG electrode unit 110 is the EMG electrode unit 110*b* of FIG. 2B.

In an embodiment, the first FES electrode 151, the EMG electrode unit 110*b*, and the second FES electrode 152 may be disposed to be spaced apart along a first direction. The EMG electrode unit 110 may be disposed between the first FES electrode 151 and the second FES electrode 152. The arrangement of the electrode unit 160 is an example, and the scope of the present disclosure is not limited thereto.

In an embodiment, as illustrated in FIG. 11, the P electrode 111*b* and the R electrode 114*b* may be disposed to be spaced apart from each other along the first direction. The N1 electrode 112*b* and the N2 electrode 113*b* may be disposed to be spaced apart from each other along a second direction. The N1 electrode 112*b* and the N2 electrode 113*b* may be disposed between the P electrode 111*b* and the R electrode 114*b* along the first direction. The P electrode 111*b* and the R electrode 114*b* may be disposed between the N1 electrode 112*b* and the N2 electrode 113*b* along the second direction. That is, the P electrode 111*b*, the N1 electrode 112*b*, the R electrode 114*b*, and the N2 electrode 113*b* may be sequentially disposed at the vertices of a rhombus shape in a counterclockwise direction. The arrangement of the EMG electrode unit 110*b* is an example, and the scope of the present disclosure is not limited thereto.

In an embodiment, by making the distance between the plurality of electrodes 111*b* to 114*b* adjacent, signal interference due to surrounding muscles may be reduced. For example, the surrounding muscle refers to a muscle adjacent to the control target muscle. That is, by reducing the physical arrangement interval between the plurality of electrodes 111*b* to 114*b*, it is possible to minimize the influence of the remaining muscles other than the control target muscle. That is, the EMG electrode unit 110 may detect a high-quality EMG signal.

Figure 12A:
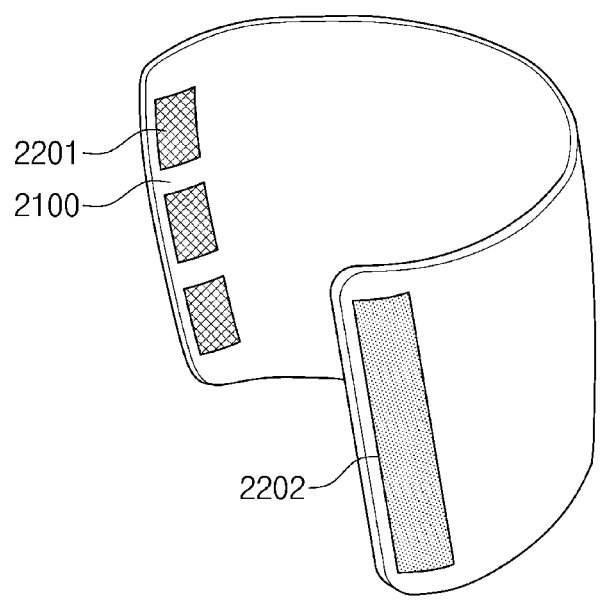
FIGS. 12A to 12C are diagrams illustrating a protector according to an embodiment of the present disclosure.
Figure 12B:
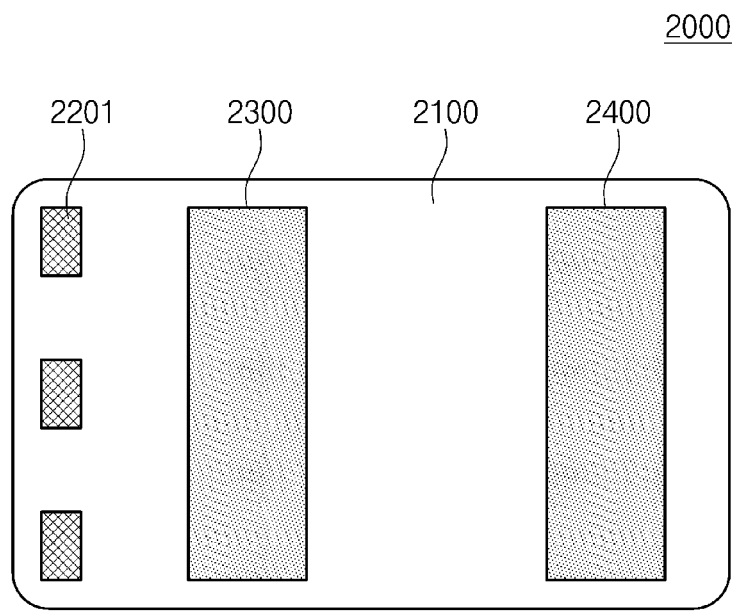
Figure 12C:
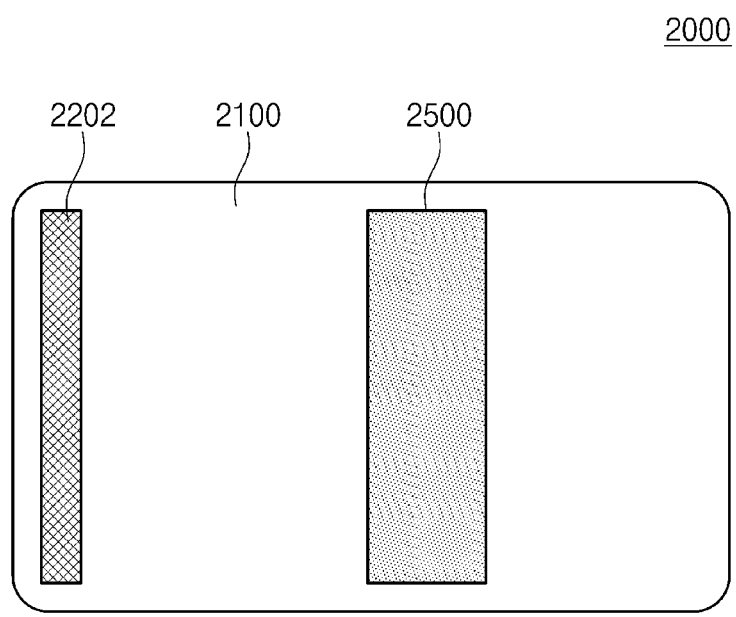

FIGS. 12A to 12C are diagrams illustrating a protector according to an embodiment of the present disclosure. FIG. 12A illustrates a perspective view of a protector 2000, FIG. 12B illustrates a plan view of the rear side in a state where the protector 2000 is unfolded, and FIG. 12C illustrates a plan view of the front side in the state where the protector 2000 is unfolded.

The protector 2000 may include a wearing unit 2100 to be worn on a part of the user's body. The wearing unit 2100 may include a belt-type body and fastening parts 2201 and 2202 provided at both ends of the body so as to be worn on the user's thigh or calves. The fastening parts 2201 and 2202 may be made of a material such as Velcro, and thus may be easily detached. For example, the protector 2000 may be worn on the thigh or calf of the user to control muscles such as anterior tibialis anterior, gastrocnemius, rectus femoris, biceps femoris, etc. The scope of the present disclosure is not limited thereto, and the protector 2000 may be worn at any position requiring muscle control or rehabilitation.

Referring to FIG. 12B, the protector 2000 may include a first electrode unit 2300 and a second electrode unit 2400 that are in close contact with the user's skin. The first electrode unit 2300 and the second electrode unit 2400 may be positioned or contacted with a part of the skin of the user's calf or thigh. The first electrode unit 2300 may control the first muscle, and the second electrode unit 2400 may control the second muscle.

The first electrode unit 2300 and the second electrode unit 2400 may include an EMG electrode unit and an FES electrode unit, like the electrode unit described above. The first electrode unit 2300 and the second electrode unit 2400 may sense the EMG signal of the control target muscle by the method described with reference to FIGS. 1 to 11 and may transfer the FES according to the motion intention.

Referring to FIG. 12C, the protector 2000 may include a circuit board unit 2500. The circuit board unit 2500 may include an EMG circuit unit and an FES circuit unit, like the circuit board unit described above. However, unlike the circuit board unit described above, the circuit board unit 2500 may receive the EMG electrode signals from the first electrode unit 2300 and the second electrode unit 2400, respectively, and may transfer the corresponding FES signal. That is, the first and second electrode units 2300 and 2400 may share the circuit board unit 2500.

Figure 13:
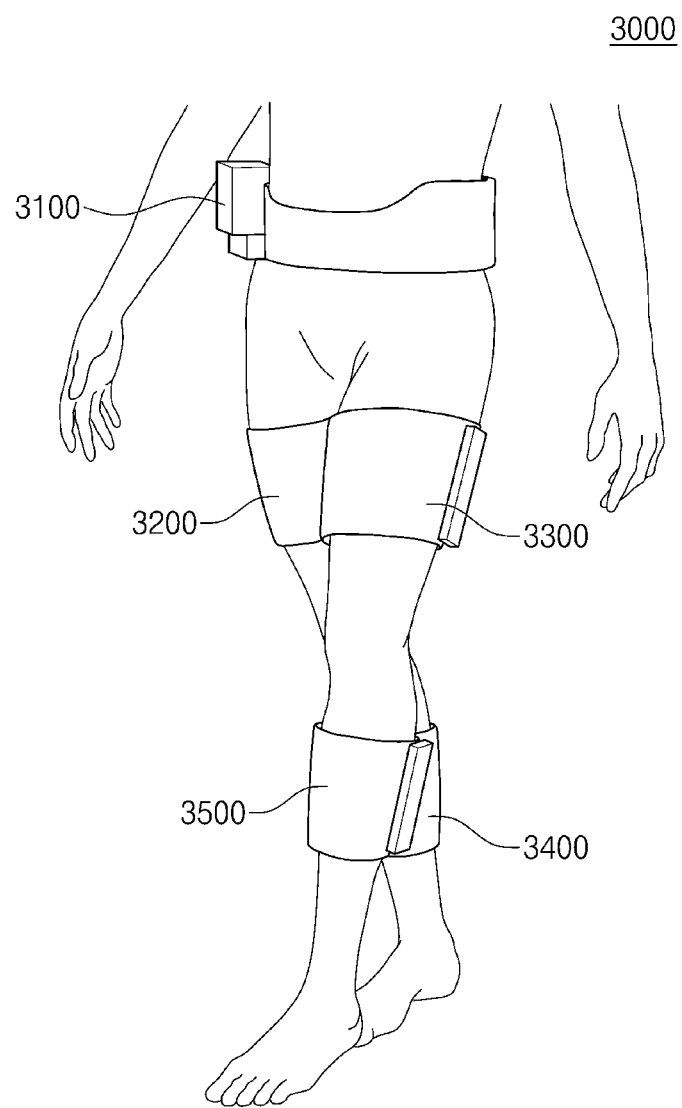
FIG. 13 is a diagram illustrating a user wearing a protector of FIG. 12.

FIG. 13 is a diagram illustrating a user wearing a protector of FIG. 12. Referring to FIGS. 12 and 13, the user may wear a control unit 3100 on the waist. The user may wear a first protector 3200 on the first thigh, may wear a second protector 3300 on the second thigh, may wear a third protector 3400 on the first calf, and may wear a fourth protector 3500 on the second calf.

The first to fourth protectors 3200 to 3500 may be protectors described in FIG. 12. The control unit 3100 may receive the EMG channel data obtained from the first to fourth protectors 3200 to 3500, respectively. The control unit 3100 may independently determine the FES stimulation parameters of each of the plurality of muscles, based on the received channel data. The control unit 3100 may transmit the determined FES stimulation parameters to the first to fourth protectors 3200 to 3500. Like the control unit of FIG. 9, the control unit 3100 may independently control a plurality of control target muscles. The control unit 3100 may independently control a plurality of control target muscles in the manner described with reference to FIGS. 1 to 11.

The contents described above are specific embodiments for implementing the present disclosure. The present disclosure may include not only the embodiments described above but also embodiments in which a design is simply or easily capable of being changed. In addition, the present disclosure may also include technologies easily changed to be implemented using embodiments. Therefore, the scope of the present disclosure is not limited to the described embodiments but should be defined by the equivalents of the claims as well as the claims to be described later.

INDUSTRIAL APPLICABILITY

The present disclosure relates to a muscle control device. In more detail, the present disclosure may be used in a muscle control device and an operation method thereof that reflect a motion intention of a user.

The invention claimed is:
1. A muscle control device comprising:
an electromyography (EMG) electrode unit including a plurality of electrodes, and configured to sense an EMG signal;
an EMG circuit unit configured to generate channel data, based on electrode signals received from the EMG electrode unit;
a control circuit unit configured to receive the channel data from the EMG circuit unit, to extract a volitional electromyography signal, based on the channel data, and to determine FES (Functional Electrical Stimulation) stimulation parameters, based on the volitional electromyography signal;

an FES electrode unit configured to output a functional electrical stimulation, based on the FES stimulation parameters; and an FES circuit unit configured to receive the FES stimulation parameters from the control circuit unit, to generate the functional electrical stimulation, based on the FES stimulation parameters, and to transmit the functional electrical stimulation to the FES electrode unit, and wherein the control circuit unit adjusts an intensity of the functional electrical stimulation, based on the volitional electromyography signal, wherein the control circuit unit determines whether a user is performing a periodic action, wherein when it is determined that the user is performing the periodic action, the control circuit unit adjusts a timing of the FES to match, precede, or lag behind a timing of the EMG signal.

2. The muscle control device of claim 1, wherein the control circuit unit generates an EMG effective value by performing a root mean square operation on the volitional electromyography signal, and determines the FES stimulation parameters such that the intensity of the functional electrical stimulation increases as the EMG effective value increases.

3. The muscle control device of claim 2, wherein values of the FES stimulation parameters are proportional or inversely proportional to the EMG effective value.

4. The muscle control device of claim 2, wherein the FES stimulation parameters are a combination of a pulse magnitude, a pulse period, a pulse width, and a pulse shape.

5. The muscle control device of claim 2, wherein the channel data include first channel data and second channel data, and wherein the control circuit unit extracts first channel previous period data and second channel previous period data during a first period, extracts first channel current period data and second channel current period data during a second period, generates first channel difference calculation data by performing a difference calculation on the first channel previous period data and the first channel current period data, generates second channel difference calculation data by performing a difference calculation on the second channel previous period data and the second channel current period data, and extracts the volitional electromyography signal by performing a difference calculation on the first channel difference calculation data and the second channel difference calculation data.

6. The muscle control device of claim 5, wherein the EMG signal is a signal in which a stimulation artifact, an M-wave, and the volitional electromyography signal are combined, which are caused by the functional electrical stimulation.

7. The muscle control device of claim 1, wherein a user's intention including a direction of a motion or a strength of a force is identified based on the volitional electromyography signal.

8. The muscle control device of claim 7, wherein the control circuit unit communicates with the EMG circuit unit and the FES circuit unit, based on any one of a UART (universal asynchronous receiver-transmitter), an SPI (serial peripheral interface), an I2C (inter-integrated circuit), a Bluetooth, a USB (Universal Serial Bus), or a WiFi.

9. A method of operating a muscle control device, the method comprising:

sensing an EMG (Electromyography) signal through a plurality of electrodes;

extracting a volitional electromyography signal based on the EMG signal;

determining whether a user is performing a periodic action;

adjusting a timing of an FES (Functional Electrical Stimulation) to match, precede, or lag behind a timing of the EMG signal, when it is determined that the user is performing the periodic action;

determining FES stimulation parameters based on the volitional electromyography signal; and outputting a functional electrical stimulation, based on the FES stimulation parameters, and wherein an intensity of the functional electrical stimulation is adjusted based on the volitional electromyography signal.

10. The method of claim 9, wherein the determining of the FES stimulation parameters based on the volitional electromyography signal includes:

generating an EMG effective value by performing a root mean square operation on the volitional electromyography signal; and determining values of the FES stimulation parameters to be proportional to the EMG effective value.

11. The method of claim 10, wherein the EMG effective value is proportional to a force applied by the user's intention to move a joint.

12. The method of claim 10, wherein the determining of the FES stimulation parameters based on the volitional electromyography signal further includes:

adjusting the values of the FES stimulation parameters such that the intensity of the functional electrical stimulation is proportional to the EMG effective value.

13. The method of claim 9, wherein the extracting of the volitional electromyography signal based on the EMG signal includes removing effects of a stimulation artifact and an M-wave, which are generated by the functional electrical stimulation, from the sensed EMG signal.

14. The method of claim 9, wherein the adjusting of the timing of the FES includes adjusting the timing of the FES, based on information acquired using a foot switch, an inertia measurement unit (IMU) sensor, or a goniometer.

* * * * *